United States Patent
Otaki et al.

[11] 3,992,419
[45] Nov. 16, 1976

[54] METHOD OF PREPARING MALEIC ANHYDRIDE AND CATALYSTS UTILIZED THEREFOR

[75] Inventors: Tadaaki Otaki, Komae; Naoto Wada, Yokohama; Masakatu Hatano, Machida, all of Japan

[73] Assignee: Mitsubishi Kasei Kogyo Kabushiki Kaisha, Japan

[22] Filed: Apr. 21, 1975

[21] Appl. No.: 569,669

[30] Foreign Application Priority Data
Apr. 19, 1974 Japan................................ 49-44274
Dec. 27, 1974 Japan.................................... 49-597

[52] U.S. Cl........................... 260/346.8 A; 252/435; 252/437
[51] Int. Cl.²................. C07D 307/60; B01J 27/14
[58] Field of Search.............. 260/346.8 A; 252/435, 252/437

[56] References Cited
UNITED STATES PATENTS

| | | | |
|---|---|---|---|
| 1,956,482 | 4/1934 | Zumstein | 260/346.8 A |
| 3,156,705 | 11/1964 | Kerr | 260/346.8 A |
| 3,293,290 | 12/1966 | Flint | 260/346.8 A |
| 3,639,269 | 2/1972 | Koberstein | 252/437 |
| 3,642,930 | 2/1972 | Grasselli | 252/437 |
| 3,862,146 | 1/1975 | Boghosian | 260/346.8 A |

*Primary Examiner*—Patrick P. Garvin
*Assistant Examiner*—John F. Niebling
*Attorney, Agent, or Firm*—Oblon, Fisher, Spivak, McClelland & Maier

[57] ABSTRACT

In a method of preparing maleic anhydride by oxidizing an unsaturated hydrocarbon or a mixture of unsaturated hydrocarbons having 4 or more carbon atoms in each molecule, there is used a catalyst comprising a mixed or complex oxide having the chemical composition:

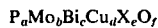

$$P_aMo_bBi_cCu_dX_eO_f$$

where X represents one or more members selected from the group consisting of iron, cobalt, nickel and potassium or the group consisting of iron, cobalt and nickel; $a$, $b$, $c$, $d$, $e$ and $f$ represent the number of atoms of P, Mo, Bi, Cu and O, respectively, $e$ represents the sum of the number of atoms of the member or members represented by X; and the value of $f$ is determined by the values of $a$, $b$, $c$, $d$ and $e$ and the valencies of P, Mo, Bi, Cu and O. Further addition of an alkali and/or alkaline earth metal as a component in the catalyst results in the improvement of the activity of the catalyst. Alkali and alkaline earth metals selected from the group Li, Na, Rb, Cs, Be, Mg, Ca, Sr and Ba are useful for the present purpose.

22 Claims, No Drawings

METHOD OF PREPARING MALEIC ANHYDRIDE AND CATALYSTS UTILIZED THEREFOR

BACKGROUND OF THE INVENTION

1. Field of the Invention

This invention relates to a method of preparing maleic anhydride; more particularly, in the improvment of the catalysts utilized for preparing maleic anhydride.

2. Description of the Prior Art

In preparing maleic anhydride by the catalytic oxidation of unsaturated hydrocarbons containing 4 or more carbon atoms in each molecule, phosphorus-vanadium-oxygen type catalysts are typically used. Although catalysts of this type can produce maleic anhydride in high yields when the concentration of the starting material unsaturated hydrocarbon is low, they are not fully satisfactory because the yield of the maleic anhydride is decreased as the concentration of the raw material is increased. A similar disadvantage is also encountered when catalysts consisting of oxides of molybdenum or antimony are used. An example of such a catalyst consisting of molybdenum containing oxides is disclosed in Japanese Patent Publication No. 685/1972. The catalyst disclosed therein has the general composition:

$$V_nP_bMo_cNi_dFe_eBi_fX_gO_h$$

where X represents magnesium and/or cobalt, and $a$, $b$, $c$, $d$, $e$, $f$, $g$ and $h$ represent the number of atoms of vanadium, phosphorus, molybdenum, nickel, iron, bismuth, magnesium and/or coablt, respectively. When these molybdenum or antimony containing oxides are used as catalysts, it is necessary to decrease the concentration of the starting material unsaturated hydrocarbons to an extremely low value; to use pure oxygen as an oxidizing agent; or to supply a large volume of steam into the reaction system. For this reason, it is difficult to use these catalysts on an industrial scale and a need exists for an industrially suitable catalyst.

SUMMARY OF THE INVENTION

Accordingly, it an object of this invention to provide novel catalysts capable of preparing maleic anhydride in high yields on an industrial scale.

Another object of this invention is to provide a novel method of preparing maleic anhydride in high yields from a raw material gas containing unsaturated hydrocarbons independent of the concentration of the latter.

Briefly, these and other objects of the invention as will hereinafter be made clear from the ensuing discussion have been achieved by providing a method of preparing maleic anhydride which comprises the step of contact oxidation, at a reaction temperature of from 250° – 550° C, of an unsaturated hydrocarbon containing 4 or more carbon atoms, with oxygen using a catalyst comprising a mixed or complex oxide expressed by the general formula $$P_aMo_bBi_cCu_dX_eO_f \quad (1)$$

where P, Mo, Bi, Cu and O represent phosphorus; molybdenum, bismuth, copper, and oxygen, respectively; X represents one or more members selected from the group consisting of iron, cobalt, nickel and potassium or the group consisting of iron, cobalt and nickel; $a$, $b$, $c$, $d$ and $f$ represent the number of atoms of said phosphorus, molybdenum, bismuth, copper and oxygen, respectively; $e$ represents the sum of the number of atoms of the member or members represented by X; and the value of $f$ is determined by the values of $a$, $b$, $c$, $d$ and $e$ and the valencies of P, Mo, Bi, Cu and O. It is preferred that $b = 12$, $a = 0.05 - 10$, $c = 0.05 - 5$, $d = 0.01 - 5$ and $e = 0.01 - 15$; it is more preferred that $b = 12$, $a = 0.1 - 4$, $c = 0.1 - 3$, $d = 0.01 - 3$ and $e = 0.01 - 10$; and it is still more preferred than $b = 12$, $a = 0.01 - 10$, $c = 0.1 - 3$, $d = 0.03 - 1$ and $e = 0.05 - 5$ or that $b = 12$, $a = 0.5 - 7$, $c = 0.1 - 2$, $d = 0.03 - 0.5$ and $e = 0.05 - 2$.

Even further improved activity is effected by the addition of alkaline and/or alkaline earth metals into the catalyst described in the general formula (1). Those metals selected from the group of Li, Na, Rb, Cs, Be, Mg, Ca, Sr and Ba are useful for the present purpose. In this case the catalyst can be described by the following general formula:

$$P_aMo_bBi_cCu_dX_eY_gO_f \quad (2)$$

Here, X represents one or more of Fe, Co and Ni; Y represents at least one member selected from the group consisting of Li, Na, Rb, Cs, Be, Mg, Sr and Ra. Letters $a$, $b$, $c$, $d$, $e$, $f$ and $g$ prescribe the composition of the elements in the general formula (2). Acceptable values for $a$, $b$, $c$, $d$, $e$, and $g$ are, respectively ($b$ is normalized to 12); $a = 0.05 - 10$, $b = 12$, $c = 0.05 - 5$, $d = 0.01 - 5$, $e = 0.01 - 15$ and $g = 0.05 - 5$. The value $f$ is determined by the values of $a$, $b$, $c$, $d$, $e$ and $g$ and the valencies of each element contained in the oxide. More preferably, the values $a$, $b$, $c$, $d$, $e$ and $g$ in the general formula (2) should be selected from the values in the following ranges ($b$ is normalized to 12): $a = 0.1 - 10$, $b = 12$, $c = 0.1 - 3$, $d = 0.03 - 1$, $e = 0.05 - 5$ and $g = 0.1 - 4$; and more preferably, $b = 12$, $a = 0.5 - 7$, $c = 0.1 - 2$, $d = 0.03 - 0.5$, $e = 0.05 - 2$ and $g = 0.5 - 4$.

DESCRIPTION OF THE PREFERRED EMBODIMENTS

In preparing the catalyst of the present invention, suitable sources of phosphorus include the various phosphoric acids and various organic and inroganic phosphorus compounds. Suitable molybdenum sources include the various molybdates, molybdenum oxides and molybdic acids. Suitable bismuth sources include various salts such as bismuth nitrate, and bismuth oxide and the like; while suitable copper sources include salts such as copper nitrate and the like, copper oxides, copper complexes and metallic copper. Suitable sources of iron, cobalt and nickel include their respective salts, oxides and complexes thereof. Also included are compounds thereof which can be converted into the respective oxides when heated under an oxygen atmosphere, or metallic iron, metallic cobalt, and metallic nickel. Suitable alkaline or alkaline earth metal sources include the various inorganic salts of alkaline or alkaline earth metals such as the nitrates, chlorides and salts of various organic acids.

In preparing the catalyst of the present invention, various methods and orders of addition of the raw materials are acceptable. For example, aqueous solutions of phosphoric acid, ammonium molybdate and bismuth nitrate in dilute nitric acid can be mixed together at room temperature to form a precipitate which is then dried and calcined to produce a mixed oxide containing phosphorus, molybdenum and bismuth. The mixed oxide is then suspended in an aqueous solution containing nitrites of iron, cobalt, nickel, copper, alkali metals and/or alkaline earth metals in order to dope the oxide with those metals. It is then dried and calcined again. Alternatively, after stirring the suspension of the mixed oxide in an aqueous solution of the salts of iron, cobalt and/or nickel, the resulting mixture may be heated to remove water, powdered and then added to an aqueous solution of the salts of alkaline and/or alkaline earth metals. Finally, it is dried and calcined under an oxygen atmosphere. Furthermore, it also is possible to mix together all the aqueous solutions (or if desired solutions in suitable solvents) of the salts or acids of the elements to be used, and then to dry and calcine the resulting precipitate or condensate.

Of course, the catalyst may either be supported or unsupported. However, it is advantageous to use an inexpensive support such as silica, titania, alumina, silicon carbide, etc. A proper mixture of silica and titania is especially useful as the support because it produces a catalyst which has a higher attrition resistance and is highly active. Although the weight ratio of the catalytic components to the support in the supported catalyst can vary depending upon the type of the mixed oxide and the support to be used, ratios of 80 – 20 : 20 – 80 are advantageous. In these ratios, the sum of the weights of the catalyst and the support is taken as 100.

The calcination temperature for preparing the catalyst ranges from 250° – 650° C, preferably from 300° – 600° C under an oxygen atmosphere. It is simple and efficient to calcine the catalyst in an air flow.

Suitable hydrocarbons for oxidation to maleic anhydride by the method of the present invention include unsaturated hydrocarbons containing four or more carbon atoms in each molecule. Preferred examples thereof include butene-1, butene-2, butadiene, pentane, pentadiene, cyclopentadiene and benzene. These unsaturated hydrocarbons may be used alone or as mixtures of two or more different hydrocarbons. Presence of a saturated hydrocarbon or unsaturated hydrocarbon containing less than four carbons such as ethylene and propylene, along with the unsaturated hydrocarbons or mixtures thereof is not harmful to the process of this invention. Accordingly, such mixtures can also be used in this invention. Thus, for example $C_4$, $C_5$. . . distillates obtained by the pyrolysis of petroleum naphtha or natural gas may be used as is or after suitable separation and purification.

Suitable oxidizing agents include pure oxygen or oxygen diluted with nitrogen, a saturated hydrocarbon and/or steam. However, the use of air is most simple and economical. The preferred concentration of the raw material in the feed gas is about 0.1 to 6% by volume. 1 to 5% by volume is most advantageous.

It is possible to use the catalyst of the present invention in any one of the many types of presently used reactors including a fluidized bed and fixed bed. Although the reaction temperature varies depending upon the type of olefin and catalyst employed, it usually ranges from 250° – 550° C, preferably from 300° – 500° C. The space velocity of the gas in the reactor should be in the range of from 100 to 10,000 $hr^{-1}$.

Having generally described the invention, a more complete understanding can be obtained by reference to certain specific examples, which are included for purposes of illustration only and are not intended to be limiting unless otherwise specified. The reaction temperatures disclosed in each of the following examples were selected from temperature zones that give substantially the maximum yield under each set of reaction conditions.

EXAMPLE 1

An aqueous solution prepared by dissolving 8.7 g of bismuth nitrate ($Bi(NO_3)_3 \cdot 5H_2O$) in 25 ml of 25% nitric acid was added dropwise into an aqueous solution prepared by dissolving 106.08 g of ammonium molybdate (($NH_4)_6Mo_7O_{24} \cdot 4H_2O$) in 500 ml of desalted water. While stirring the resulting solution containing a white precipitate at room temperature, a solution prepared by diluting 5.8 g of 85% phosphoric acid with about 15 ml of desalted water was added. After drying on an electric heater, the resulting pale yellow solid was ground, pressed into discs and finally was calcined at 400° C for 2 hours in an air flow. 13.2 g of the mixed oxide thus obtained containing phosphorus, molybdenum and bismuth, was pulverized into a fine powder in a mortar. The fine powder was impregnated with an aqueous solution obtained by dissolving 1.45 g of ferric nitrate ($Fe(NO_3)_3 \cdot 9H_2O$) in approximately 20 ml of desalted water and the impregnated powder was then dried and pressed into discs (6mm $d \times$ 2mm thickness). The discs thus obtained were calcined for 2 hours at 400° C in an air flow. 10.8 g of the resulting mixed oxide containing phosphorus, molybdenum, bismuth and iron was again impregnated with 10 ml of an aqueous solution containing 0.24 g of copper nitrate ($Cu(NO_3)_2 \cdot 3H_2O$) and then dried and pressed into discs and calcined for 2 hours at 400° C in air flow. In view of the method of preparation, the resulting mixed oxide containing phosphorus, molybdenum, bismuth, copper and iron had the chemical composition: $P_1Mo_{12}Bi_{0.36}Cu_{0.18}Fe_{0.52}O_{40.0}$.

The catalyst thus obtained was set in a small size fixed bed reactor and butene-1 diluted with air to a concentration of 4.0% by volume was passed through the reactor at a space velocity of 2,500 $hr^{-1}$ while the catalyst bed was maintained at a temperature of 350° C. Total conversion of butene-1 was 100%, and the yield of maleic anhydride was 37.5%. The sum of the yields of acetic acid and acrylic acid was 14.8%.

EXAMPLE 2

In a manner similar to that of Example 1, a complex oxide containing phosphorus, molybdenum and bismuth was prepared. The complex oxide was then impregnated with a predetermined amount of cobalt nitrate ($Co(NO_3)_2 \cdot 6H_2O$) to obtain a mixed oxide containing phosphorus, molybdenum, bismuth and cobalt which was in turn was impregnated with copper nitrate. The impregnated mixed oxide was then pressed into discs (6mm $d \times$ 2 mm thickness) and calcined at a temperature of 400° C in an air flow to obtain a mixed oxide containing phosphorus, molybdenum, bismuth, copper and cobalt which was assumed to have a chemical composition of $P_1Mo_{12}Bi_{0.36}Cu_{0.18}Co_{0.52}O_{39.7}$ in view of its method of preparation.

The catalyst thus obtained was used to oxidize butene-1 which had been diluted with air to a concentration of 4.0% by volume under the same conditions as in Example 1, except that the reaction temperature was changed to 385° C. The yield of maleic anhydride was 35.5% while the sum of the yields of acrylic acid and acetic acid was 9.2%.

EXAMPLE 3

In the same manner as in Example 1, a mixed oxide containing phosphorus, molybdenum and bismuth was prepared. The mixed oxide was impregnated with a predetermined amount of nickel nitrate ($Ni(NO_3)_2\cdot 6H_2O$), then pressed into discs and calcined to obtain a mixed oxide containing phosphorus, molybdenum, bismuth aand nickel. Thereafter, the complex oxide thus obtained was impregnated with a predetermined amount of copper nitrate, pressed into discs and calcined at 400° C in an air flow to obtain a mixed oxide containing phosphorus, molybdenum, bismuth, copper and nickel which was assumed to have a chemical composition of $P_1Mo_{12}Bi_{0.36}Cu_{0.18}Ni_{0.52}O_{39.7}$ in view of the method of preparation. The catalyst thus obtained was used to oxidize butene-1 diluted with air to a concentration of 4.0% by volume under the same conditions as in Example 1 except that the reaction temperature was changed to 365° C. The percentage of conversion of butene-1 was 99%, the yield of maleic anhydride was 36.5% and the sum of the yields of acetic acid and acrylic acid was 11.6%.

EXAMPLE 4

53.0 g of ammonium molybdate was dissolved in 250 ml of desalted water. Into the stirred solution, at room temperature, 12.5 ml of 25% nitric acid solution containing 4.4 g of bismuth nitrate, an aqueous solution prepared by dissolving 2.9 g of 85% phosphoric acid in 20 ml of desalted water, and an aqueous solution prepared by dissolving a mixture consisting of 1.24 g of cobalt nitrate, 1.72 g of ferric nitrate, 1.24 g of nickel nitrate and 0.61 g of copper nitrate in 50 ml of desalted water were added dropwise in the order in which then have been mentioned. The solution containing the precipitate was concentrated by heating and dried in an oven maintained at a temperature of 150° C for 20 hours. After drying, the powder was pressed into discs and then calcined for 2 hours at 400° C in an air flow. The catalyst thus obtained was assumed to have a chemical composition of $P_1Mo_{12}Bi_{0.36}Cu_{0.10}Fe_{0.17}Co_{0.17}Ni_{0.17}O_{39.7}$.

The catalyst was set in a small size fixed bed reactor and butene-1 diluted with air to a concentration of 4.0% by volume was passed at a space velocity of 2,500 $hr^{-1}$ while the rection temperature was maintained at 384° C. The percentage conversion of butene-1 was 100%, the yield of maleic anhydride was 41.3% and the sum of the yields of acetic acid and acrylic acid was 17.3%.

EXAMPLE 5

In this example, 53.0 g of ammonium molybdate was dissolved in 250 ml of desalted water. Into the stirred solution, at room temperature, a solution prepared by dissolving 4.4 g of bismuth nitrate in 12.5 ml of 25% nitric acid, an aqueous solution prepared by dissolving 2.9 g of 85% phosphoric acid in 20 ml of desalted water, and an aqueous solution prepared by dissolving a mixture consisting of 1.24 g of cobalt nitrate, 1.72 g of ferrous nitrate, 1.24 g of nickel nitrate, 0.61 g of copper nitrate, and 0.13 g of potassium nitrate in 50 ml of desalted water were added dropwise in the order in which they have been mentioned. The resulting aqueous solution containing the precipitate was concentrated by heating and then dried in an oven maintained at a temperature of 150° C for 20 hours. The powder thus obtained was pressed into discs and then calcined for 2 hours at a temperature of 400° C in an air flow.

It is presumed that the mixed oxide prepared in this manner had a chemical composition of $P_1Mo_{12}Bi_{0.36}Cu_{0.10}Fe_{0.17}Co_{0.17}Co_{0.17}Ni_{0.17}K_{0.05}O_{39.8}$ in view of the method of preparation thereof.

The mixed oxide was set in a small size fixed bed reactor and butene-1 diluted with air to a concentration of 4.0% by volume was introduced at a space velocity of 2,500 $hr^{-1}$ while maintaining the reaction temperature at 370° C. The percentage conversion of butene-1 was 100%, the yield of maleic anhydride was 41.5% and the sum of yields of acetic acid and acrylic acid was 8.2%.

EXAMPLE 6

The same catalyst as in Example 5 was used to oxidize 1,3-butadiene. The catalyst was set in a small fixed bed reactor and while maintaining the temperature of the catalyst bed at 400°C, 1,3-butadiene diluted with air to a concentration of 4% by volume was introduced at a space velocity of 2,500 $hr^{-1}$. The precentage conversion of 1,3-butadiene was 98%, the yield of maleic anhydride was 52.8% and the sum of the yields of acrylic acid and acetic acid was 4.6%.

EXAMPLE 7

To an aqueous solution prepared by using essentially the same amounts of the same reagents as those mentioned in Example 4 and containing a precipitate were added 42.0 g of an anatase type titania previously calcined at a temperature of 1,000° C and 85.7 g of 35% aqueous suspension of silica sol under vigorous stirring. The mixture was further stirred for about one hour at room temperature. Then the mixture was concentrated by heating and dried in an oven maintained at 150°C for 15 hours. The resulting powder was pressed into discs and was calcined for 2 hours at 400°C in an air flow. It is expected that the catalyst thus obtained had a chemical composition similar to that of Example 4 in view of the method of preparation. The catalyst consisted of 40% by weight of the active component as catalyst, 35% by weight of titania and 25% by weight of silica.

The supported catalyst was set in a small size fixed bed reactor and butene-1 diluted with air to a concentration of 4.0% by volume was introduced at a space velocity of 2,500 $hr^{-1}$. The precentage conversion of butene-1 was 100%, the yield of maleic anhydride was 41.2% and the sum of the yields of acrylic acid and acetic acid was 15.3%.

EXAMPLE 8

The same catalyst as in Example 5 was used to oxidize butene-1 which had been diluted with air to a concentration of 2.0% by volume. While maintaining the temperature of the catalyst bed at a temperature of 370°to C, the diluted butene-1 was introduced into the reactor. The percentage conversion of butene-1 was 100%, the yield of maleic anhydride was 48.2% and the sum of the yields of acrylic acid and acetic acid was 10.5%.

CONTROL EXAMPLE 1

A catalyst having a composition similar to that of Example 1 but not containing copper was prepared by a method similar to Example 1. In view of the method of preparation it was presumed that the catalyst had a chemical composition of $P_1Mo_{12}Bi_{0.36}Fe_{0.52}O_{39.8}$. With this catalyst, a reaction was carried out under the same conditions as in Example 1. It was found that the reaction temperature which gives the maximum yield of maleic anhydride was 375° C and that the yield of maleic anhydride at this temperature was 35.0%.

CONTROL EXAMPLE 2

A catalyst having a composition similar to that of Example 3 but not containing copper was prepared by a method similar to that of Example 3. In view of the method of preparation it was presumed that the catalyst had a chemical composition of $P_1Mo_{12}Bi_{0.36}Ni_{0.52}O_{39.5}$. This catalyst was used to oxidize butene-1 under the same conditions as in Example 3. It was found that the reaction temperature which gives the maximum yield of maleic anhydride was 345° C, and that the yield of maleic anhydride at this temperature was 28.0%.

CONTROL EXAMPLE 3

A catalyst having a composition similar to that of Example 4 but not containing copper was prepared by a method similar to that of Example 4. In view of the method of preparation, it was presumed that the catalyst thus obtained had a chemical composition of $P_1Mo_{12}Bi_{0.36}Fe_{0.17}Ni_{0.17}O_{39.6}$. When the catalyst was used for oxidizing butene-1 under the same conditions as in Example 4, the reaction temperature which gives the maximum yield of maleic anhydride was found to be 440° C and the yield of maleic anhydride at this temperature was 37.5%.

EXAMPLE 9

An aqueous solution prepared by dissolving 2.2 g of bismuth nitrate $(Bi(NO_3)_3 \cdot 5H_2O)$ in 6.5 ml of 25% nitric acid was added dropwise into an aqueous solution prepared by dissolving 26.5 g of ammonium molybdate in 60 ml of desalted water. While stirring the resulting solution containing a white precipitate at room temperature a solution prepared by diluting 3.2 g of 85% phosphoric acid with about 10 ml of desalted water was added dropwise. While stirring the resulting slurry, an aqueous solution prepared by dissolving a mixture consisting of 6.2 g of cobalt nitrate $(CO(NO_3)_2 \cdot 6H_2O)$, 0.86 g of ferric nitrate $(Fe(NO_3)_3 \cdot 9H_2O)$, 0.62 g of nickel nitrate $(Ni(NO_3)_2 \cdot 6H_2O)$ and 0.31 g of copper nitrate $(Cu(NO_3)_2 \cdot 3H_2O)$ in 15 ml of desalted water was added dropwise into the slurry. After continuing the stirring for 30 minutes, 43.1 g of silica sol (containing 35% by weight of $SiO_2$ and 0.65% by weight of sodium oxide) and 21.1 g of titania were added to the slurry in the order in which they have been mentioned, and the resulting mixture was stirred for about 20 minutes at room temperature. The resulting slurry was dried on an electric heater while stirring to obtain a solid mass which was then pulverized in a magnetic mortar. The powder was then pressed into discs and was calcined for two hours at a temperature of 400° C in an air flow to obtain a catalyst. In view of the method of preparation, this catalyst (excluding the carrier) was assumed to have a chemical composition of $P_{2.21}Mo_{12}Bi_{0.36}Cu_{0.10}Fe_{0.17}Co_{0.17}Ni_{0.17}Na_{0.60}O_{0.30}$. The weight ratio of the active component of the catalyst to the carrier component was 40:60.

The catalyst thus obtained was set in a small size fixed bed reactor and while maintaining the temperature of the catalyst bed at 370° C, a mixture of $C_4$ hydrocarbons diluted with air to a concentration of 4.0% by volume was introduced into the reactor at a space velocity of 2,500 $hr^{-1}$. The $C_4$ hydrocarbon mixture was constituted by 6.5% of n-butene, 16.8% of butene-1, 4.3% of trans-butene-2, 2.8% of cis-butene-2, 40.3% of 1,3-butadiene and 29.5% of isobutene, all by volume.

The percentage conversion of olefins was 100%, and the yield of maleic anhydride was 54.9%, based on the total amount of olefins admitted excluding isobutene.

EXAMPLE 10

A slurry containing phosphorus, molybdenum, bismuth, copper, iron, cobalt and nickel was prepared in a similar manner to that of Example 9 except that the amount of 85% phosphoric acid was changed to 1.45 g. While stirring, the slurry was evaporated on an electric heater and the solid thus obtained was powdered, pressed into discs and calcined in a similar manner to that of Example 9. A catalyst which was considered to have a chemical composition of $P_{1.00}Mo_{12}Bi_{0.36}Cu_{0.10}Fe_{0.17}Co_{0.17}Ni_{0.17}O_{39.7}$ was obtained. The catalyst was used to oxidize a $C_4$ hydrocarbon mixture under the same conditions as in Example 9 except that the reaction temperature was changed to 413°C. The percentage conversion of the olefins was 100% and the yield of maleic anhydride based on the total amount of olefins admitted (except isobutene) was 47.3%.

EXAMPLE 11

A slurry containing phosphorus, bismuth, copper, iron, cobalt and nickel was prepared by a method similar to that of Example 9 except that the amount of bismuth nitrate was changed to 4.4 g and that the amount of 85% phosphoric acid was changed to 2.13 g. While stirring the slurry at room temperature, an aqueous solution prepared by dissolving 1.46 g of cesium nitrate $(CsNO_3)$ in 10 ml of desalted water was added dropwise into the slurry. Then 88.6 g of silica sol (containing 20% by weight of $SiO_2$ but substantially free of sodium) and 7.6 g of titania were added to the slurry in the order mentioned and the resulting slurry was stirred for 30 minutes. The slurry thus obtained was processed in a similar manner to that of Example 9 to obtain a catalyst. In view of the method of preparation, it was assumed that the active component of this catalyst had a chemical composition of $P_{1.40}Mo_{12}Bi_{0.72}Cu_{0.10}Fe_{0.17}Co_{0.17}Ni_{0.17}Cs_{0.60}O_{41.4}$. The weight ratio of the active component of the catalyst to the support was 40:60. This catalyst was used to oxidize the $C_4$ hydrocarbon mixture under the same conditions as in Example 9, except that the reaction temperature was changed to 375° C. It was found that the percentage conversion of the olefins was 90% and the yield of maleic anhydride was 49.4% based on the total amount of olefins admitted excluding isobutene.

EXAMPLE 12

A slurry containing phosphorus, molybdenum, copper, iron, cobalt, and nickel was prepared in a similar manner as in Example 9 except that the amount of 85% phosphoric acid was changed to 4.87 g. While stirring the slurry at room temperature, an aqueous solution prepared by dissolving 1.92 g of magnesium nitrate in 10 ml of desalted water was added dropwise into the slurry. 79.1 g of silica sol (containing 20% by weight of $SiO_2$ but not containing sodium) and 22.18 g of titania were added to the slurry in the order which has been mentioned, and the stirring of the slurry was continued for 30 minutes. The resulting slurry was treated in the same manner as in Example 9 to obtain a catalyst. In view of the method of preparation, it was considered that the catalyst, excluding the support, had a chemical composition of $P_{3.35}Mo_{12}Bi_{0.36}Cu_{0.10}Fe_{0.17}Co_{0.17}Ni_{0.17}Mg_{0.60}O_{46.2}$. The weight ratio of the active component of the catalyst to the support was 40:60. This catalyst was used to oxidize a $C_4$ hydrocarbon mixture under the same conditions as in Example 9 except that the reaction temperature was changed to 380° C. The percentage conversion of olefins was 100% and the yield of maleic anhydride based on the total amount of olefins admitted excepting isobutene was 55.7%.

EXAMPLE 13

A slurry containing phosphorus, molybdenum, bismuth, copper, iron, cobalt and nickel was prepared by a method similar to that of Example 9 except that the amount of 85% phosphoric acid was changed to 4.87 g. While stirring the slurry at room temperature, a solution obtained by dissolving 1.77 g of calcium nitrate ($Ca(NO_3)_2 \cdot 4H_2O$) in 10 ml of desalted water was added dropwise into the slurry. 79.1 g of silica sol (containing 20% by weight of $SiO_2$ but not containing sodium) and 22.1 g of titania were added to the slurry in the order in which they have been mentioned and the slurry was stirred for 30 minutes. The slurry thus obtained was treated in a manner similar to that of Example 9 to obtain a catalyst. In view of the method of preparation it was assumed that the catalyst excluding the support had a chemical composition of $P_{3.35}Mo_{12}Bi_{0.36}Cu_{0.10}Fe_{0.17}Co_{0.17}Ni_{0.17}Ca_{0.60}O_{46.2}$. The weight ratio of the active component of the catalyst to the support was found to be 40:60. This catalyst was used to oxidize a $C_4$ hydrocarbon mixture under the same conditions as in Example 9 except that the reaction temperature was changed to 390° C. The percentage conversion of the olefins was 100% and the yield of maleic anhydride based on the total amount of olefins admitted (except isobutene) was 54.1%.

EXAMPLE 14

A slurry containing phosphorus, molybdenum, bismuth, copper, iron, cobalt and nickel was prepared by a method similar to that of Example 9 except that the amount of phosphoric acid was changed to 4.87 g. While stirring the slurry at room temperature, a solution prepared by dissolving 1.96 g of barium nitrate ($Ba(NO_3)_2$) in 20 ml of desalted water was added dropwise into the slurry. After stirring the slurry for about 30 minutes, 79.1 g of silica sol (containing 24% by weight of $SiO_2$ but not containing sodium) and 22.1 g of titania were added to the slurry in the order which has been mentioned, and the slurry was stirred for an additional 30 minutes. The slurry thus obtained was treated in a similar manner to that of Example 9 to obtain a catalyst. In view of the method of preparation, it was assumed that the catalyst excepting the support had a chemical composition of $P_{3.35}Mo_{12}Bi_{0.36}Cu_{0.10}Fe_{0.17}Co_{0.17}Ni_{0.17}Ba_{0.60}O_{46.2}$. The weight ratio of the active component of the catalyst to the support was 40:60. This catalyst was used to oxidize a $C_4$ hydrocarbon mixture under the same conditions as in Example 9 except that the reaction temperature was changed to 385° C. The percentage conversion of the olefins was 100% and the yield of maleic anhydride based on the total amount of olefins admitted (except isobutene) was 58.4%.

EXAMPLE 15

A slurry containing phosphorus, molybdenum, bismuth, copper, iron, cobalt, nickel and barius was prepared in the same manner as in Example 13 except that the amount of 85% phosphoric acid was changed to 7.21 g. After stirring the slurry for about 30 minutes at room temperature, 79.1 g of the same silica sol as that used in Example 13 and 22.1 g of titania were added to the slurry in the order of mention, and the slurry was stirred for an additional 30 minutes. The resulting slurry was heated in a similar manner to that of Example 9 to obtain a catalyst. In view of the method of preparation it was assumed that the catalyst except the support had a chemical composition of $P_{4.97}Mo_{12}Bi_{0.36}Cu_{0.10}Fe_{0.17}Co_{0.17}Ni_{0.17}Ba_{0.60}O_{40.3}$. The weight ratio of the active component to the support was 40:60. This catalyst was used to oxidize a $C_4$ hydrocarbon mixture under the same conditions as in Example 9 except that the reaction temperature was changed to 390° C. The percentage conversion of the olefins was 100% and the yield of the maleic anhydride based on the total amount of olefins admitted (except isobutene) was 55.5%.

EXAMPLE 16

A catalyst was prepared in a similar manner to that of Example 14 except that the amount of 85% phosphoric acid was changed to 1.45 g. Considering the method of preparation, it was assumed that the catalyst excepting the support had a chemical composition of $P_{1.00}Mo_{12}Bi_{0.36}Cu_{0.10}Fe_{0.17}Co_{0.17}Ni_{0.17}Ba_{0.60}O_{40.4}$. The weight ratio of the active component of the catalyst to the support was 40:60.

The catalyst was used to oxidize a $C_4$ hydrocarbon mixture under the same condition as in Example 9 except that the reaction temperature was changed to 376° C. The percentage conversion of the olefins was 98% and the yield of maleic anhydride based on the total amount of olefins admitted (excepting isobutene) was 53.8%.

CONTROL EXAMPLE 4

An aqueous solution prepared by dissolving 2.2 g of bismuth nitrate ($Bi(NO_3)_3 \cdot 5H_2O$) in 6.5 ml of 25% nitric acid was added dropwise into an aqueous solution prepared by dissolving 26.5 g of ammonium molybdate ($(NH_4)_6Mo_7O_{24} \cdot 4H_2O$) in 60 ml of desalted water. While stirring the resulting aqueous solution containing a white precipitate, a solution obtained by diluting 1.45 g of 58% phosphoric acid with 10 ml of desalted water was added dropwise into the resulting solution. While stirring the resulting slurry, a solution obtained by dissolving 1.67 g of copper nitrate ($Cu(NO_3)_2 \cdot 3H_2O$) in 5 ml of desalted water was added dropwise into the slurry. While stirring, the resulting soltuion containing a small quantity of a precipitate was heated on an electric heater and the solid obtained was powdered, pressed into discs and calcined as in Example 9 to obtain a catalyst which was believed to have the chemical composition of $P_{1.00}Mo_{12}Bi_{0.36}Cu_{0.54}O_{39.6}$. This catalyst was set in a reactor and butene-1 diluted with air to a concentration of 4.0% by volume was introduced into the reactor at a space velocity of 2,500 $hr^{-1}$. The percentage conversion of butene-1 was 97% but the yield of maleic anhydride based on the admitted butene-1 was only 27.9%.

Having now fully described the invention, it will be apparent to one of ordinary skill in the art that many changes and modifications can be made thereto without departing from the spirit or scope of the invention as set forth herein.

What is claimed as new and intended to be covered by letters patent is:

1. A method of preparing maleic anhydride which comprises the vapor phase oxidation of an unsaturated hydrocarbon containing at least carbon atoms in each molecule, at a reaction temperature of from 250° to 550° C in the presence of a catalyst comprising a mixed or complex oxide expressed by the general formula:

$$P_aMo_bBi_cCu_dX_eO_f$$

where P, Mo, Bi, Cu and O represent phosphorus, molybdenum, bismuth, copper and oxygen, respectively; X represents at least one member selected from the group consisting of iron, cobalt, nickel and potassium; $a$, $b$, $c$, $d$ and $f$ represent the number of atoms of said phosphorus, molybdenum, bismuth, copper and oxygen, respectively; wherein $a = 0.05$–$10$, $b = 12$, $C = 0.05$–$5$, $d = 0.01 - 5$, $e = 0.01 - 5$ and the value of f is determined by the values of said $a$, $b$, $c$, $d$ and $e$ and the valencies of each element contained in said oxide.

2. The method of claim 1, wherein X represents one or more members selected from the group consisting of iron, cobalt and nickel.

3. The method of claim 2, wherein said mixed oxide catalyst further contains at least one member selected from the group consisting of lithium, sodium, rubidium, cesium, beryllium, magnesium, calcium, strontium and barium, and is expressed by the general formula:

$$P_aMo_bBi_cCu_dX_eY_gO_f$$

wherein $a$, $b$, $c$, $d$, $e$ and $f$ have the same meanings as defined in claim 1, Y represents at least one elements selected from said group of 9 elements and $g = 0.05$–$5$.

4. The method claim 1, wherein when $b = 12$, $a = 0.1 - 10$, $c = 0.1 - 3$, $d = 0.03 -1.0$ and $e = 0.05 - 5$.

5. The method of claim 1, wherein when $b = 12$, $a = 0.1 - 4$, $c = 0.1 - 3$, $d = 0.01 - 3$ and $e = 0.01 - 10$.

6. The method of claim 1, wherein when $b = 12$, $a = 0.5 - 7$, $c = 0.1 - 2$, $d = 0.03 - 0.5$ and $e = 0.05 - 2$.

7. The method of claim 3, wherein when $b = 12$, $a = 0.1 - 10$, $c = 0.1 - 3$, $d = 0.03 - 1$, $e = 0.05 - 5$ and $g = 0.1 - 4$.

8. The method according to claim 3, wherein where $b = 12$, $a = 0.5$–$7$, $c = 0.1 - 2$, $d = 0.03 - 0.5$, $e = 0.05 - 2$ and $g = 0.5 - 4$.

9. The method of claim 2, wherein when $b = 12$, $a = 0.05 - 10$, $c = 0.05 - 5$, $d = 0.01 - 5$, and $e = 0.01 - 15$.

10. The method of claim 9, wherein when $b = 12$, $a = 0.1 - 10$, $c = 0.1 - 3$, $d = 0.03 - 1.0$ and $e = 0.05 - 5$.

11. The method of claim 9, wherein when $b = 12$, $a = 0.1 - 4$, $c = 0.1 - 3$, $d = 0.01 - 3$ and $e = 0.01 - 10$.

12. The method of claim 10, wherein when $b = 12$, $a = 0.5 - 7$, $c = 0.1 - 2$, $d = 0.03 - 0.5$, and $e = 0.05 - 2$.

13. The method of claim 1, wherein a support prepared from silica sol and titanium is used for said catalyst.

14. The method of claim 8, wherein a support prepared from silica sol and titanium is used for said catalyst.

15. The method of claim 3, wherein a support prepared from silica sol and titania is used for said catalyst.

16. The method of claim 8, wherein a support prepared from silica sol and titania is used for said catalyst.

17. A catalyst for preparing maleic anhydride by oxidizing an unsaturated hydrocarbon containing at least four carbon atoms in each molecule, said catalyst comprising a mixed or complex oxide having the chemical composition of $P_aMo_bBi_cDu_dX_eO_f$ where P, Mo, Bi, Cu and O represent phorphorus, molybdenum, bismuth, copper and oxygen, respectively; X represents at least one member selected from the group consisting of iron, cobalt, nickel and potassium; $a$, $b$, $c$, $d$ and $f$ represent the number of atoms of said phosphorus, molybdenum, bismuth, copper and oxygen, respectively; wherein $a = 0.05$–$10$, $b = 12$, $c = 0.05$–$5$, $d = 0.01$–$5$, $d = 0.01$–$5$ and $e = 0.01 - 15$, and the value of $f$ is determined by the values of said $a$, $b$, $c$, $d$ and $e$ and the valencies of said P, Mo, Bi, Cu and O.

18. The catalyst of claim 17 wherein X represents one or more members selected from the group consisting of iron, cobalt and nickel.

19. The catalyst of claim 18 which further contains at least one member selected from the group consisting of lithium, sodium, rubidium, cesium, beryllium, magnesium, calcium, strontium, and barium and expressed by the general formula:

$$P_aMo_bBi_cCu_dX_eY_gO_f$$

wherein $a$, $b$, $c$, $d$, $e$ and $f$ have the same means as defined in claim 19, Y represents at least one elements selected from said group of 9 elements and $g = 0.05$.

20. The catalyst of claim 17, wherein when $b = 12$, $a = 0.01 - 10$, $c = 0.1 - 3$, $d = 0.03 - 1.0$ and $e = 0.05 - 5$.

21. The catalyst of claim 17, wherein when $b = 12$, $a = 0.1 - 4$, $c = 0.1 - 3$, $d = 0.01 - 3$ and $e = 0.01 - 10$.

22. The catalyst of claim 20, wherein when $b = 12$, $a = 0.5 - 7$, $c = 0.1 - 2$, $d = 0.03 - 0.5$ and $e = 0.05 - 2$.

* * * * *